US010426099B2

(12) United States Patent
Clendinning et al.

(10) Patent No.: US 10,426,099 B2
(45) Date of Patent: Oct. 1, 2019

(54) METHOD FOR CONTROLLING A GROWTH CYCLE FOR GROWING PLANTS USING STATE ORIENTED CONTROL

(71) Applicant: HELIOSPECTRA AB, Göteborg (SE)

(72) Inventors: Kirk Clendinning, Jörlanda (SE); Tessa Pocock, Sundsvall (SE); Torsten Wik, Göteborg (SE)

(73) Assignee: HELIOSPECTRA AB, Göteborg (SE)

( * ) Notice: Subject to any disclaimer, the term of this patent is extended or adjusted under 35 U.S.C. 154(b) by 560 days.

(21) Appl. No.: 15/034,318

(22) PCT Filed: Nov. 6, 2014

(86) PCT No.: PCT/EP2014/073922
§ 371 (c)(1),
(2) Date: May 4, 2016

(87) PCT Pub. No.: WO2015/067691
PCT Pub. Date: May 14, 2015

(65) Prior Publication Data
US 2016/0278300 A1 Sep. 29, 2016

(30) Foreign Application Priority Data

Nov. 7, 2013 (EP) ..................................... 13191915

(51) Int. Cl.
*A01G 7/04* (2006.01)
*A01G 22/00* (2018.01)
(Continued)

(52) U.S. Cl.
CPC ............... *A01G 7/045* (2013.01); *A01G 7/00* (2013.01); *A01G 9/20* (2013.01); *A01G 22/00* (2018.02);
(Continued)

(58) Field of Classification Search
CPC . A01G 7/00; A01G 22/00; A01G 9/20; A09G 7/045
(Continued)

(56) References Cited

U.S. PATENT DOCUMENTS 5,130,545 A * 7/1992 Lussier ..................... A01G 7/00
250/458.1
7,905,052 B2 * 3/2011 Hurst ..................... A01G 7/045
47/17
(Continued)

FOREIGN PATENT DOCUMENTS

CA 2888618 A1 * 6/2014 ............. A01G 22/00
DE 10 2011 120 585 A1 6/2013
(Continued)

OTHER PUBLICATIONS

International Search Report (PCT/ISA/210) dated Feb. 9, 2015, by the European Patent Office as the International Searching Authority for International Application No. PCT/EP2014/073922.
(Continued)

*Primary Examiner* — David J Parsley
*Assistant Examiner* — Danielle A Clerkley
(74) *Attorney, Agent, or Firm* — Buchanan Ingersoll & Rooney P.C.

(57) ABSTRACT

The present invention relates to a method for controlling of a growth cycle for a plant being arranged in a controlled environment and subject to light emitted by at least one artificial lighting arrangement. The invention also relates to a corresponding system device and to a computer program product.

12 Claims, 4 Drawing Sheets

(51) Int. Cl.
*A01G 7/00* (2006.01)
*A01G 9/20* (2006.01)
*G01N 21/84* (2006.01)

(52) U.S. Cl.
CPC ............... *G01N 2021/8416* (2013.01); *G01N 2021/8466* (2013.01)

(58) Field of Classification Search
USPC .................. 47/58.1 R, 1.01 R, 17, 58.1 LS
See application file for complete search history.

(56) References Cited

U.S. PATENT DOCUMENTS

| | | | | |
|---|---|---|---|---|
| 8,074,397 | B2* | 12/2011 | Yoneda | A01G 7/045 47/1.01 R |
| 10,021,838 | B1* | 7/2018 | Gustafik | G05B 15/02 |
| 10,136,592 | B2* | 11/2018 | Broutin Farah | A01G 22/00 |
| 2003/0009933 | A1* | 1/2003 | Yoneda | A01G 7/045 47/1.01 R |
| 2004/0098911 | A1* | 5/2004 | Okamoto | G05B 23/0264 47/58.1 R |
| 2007/0289207 | A1* | 12/2007 | May | A01G 7/00 47/17 |
| 2009/0025287 | A1* | 1/2009 | Lee | A01G 7/00 47/17 |
| 2010/0263275 | A1* | 10/2010 | Anderson | A01G 25/09 47/58.1 R |
| 2012/0210644 | A1* | 8/2012 | Johnson | G06F 17/30463 47/1.01 R |
| 2013/0006401 | A1* | 1/2013 | Shan | H04L 67/125 700/90 |
| 2016/0088802 | A1* | 3/2016 | Nicole | A01G 7/045 47/58.1 LS |

FOREIGN PATENT DOCUMENTS

| | | | | |
|---|---|---|---|---|
| EP | 2 405 258 A2 | | 1/2012 | |
| EP | 2486782 A1 | * | 8/2012 | ............... A01G 7/00 |
| JP | 2002-153127 A | | 5/2002 | |
| JP | 2003-208546 A | | 7/2003 | |
| JP | 2006-333744 A | | 12/2006 | |
| JP | 2011-239703 A | | 12/2011 | |
| WO | WO 2008/118080 A1 | | 10/2008 | |

OTHER PUBLICATIONS

Written Opinion (PCT/ISA/237) dated Feb. 9, 2015, by the European Patent Office as the International Searching Authority for International Application No. PCT/EP2014/073922.

* cited by examiner

METHOD FOR CONTROLLING A GROWTH CYCLE FOR GROWING PLANTS USING STATE ORIENTED CONTROL

TECHNICAL FIELD

The present invention relates to a method for controlling a growth cycle for growing plants. Such a method may be implemented in a greenhouse, a walk-in chamber or a growth cabinet. The invention also relates to a corresponding system, use of the system and a computer program product. The invention allows for improvements in operating a greenhouse, such as in relation to reduced energy consumption and increased predictability of the growth process.

BACKGROUND OF THE INVENTION

Controlling conditions for growing plants in for example a greenhouse is of interest for optimizing plant growth. Conditions such as light, temperature, ambient water vapor pressure, $CO_2$ partial pressure, etc may be monitored and controlled in order to optimize the growth environment for the plants. Careful monitoring of growth conditions and plant response is important in order to optimize the growth environment which, if carefully tuned, may stimulate photosynthesis in the plants. Ultimately, economic returns may be affected by the outcome of the control of the growth conditions.

Control of the growth conditions may be done by a feedback control system where a status of the plant is monitored and the conditions are adjusted according to a predefined desired status of the plants. The feedback systems may then have a more or less complicated control algorithm that controls the growth conditions according to predefined schemes.

An example of a plant growth modulating system is disclosed in WO2008118080, comprising a light sensor communicatively coupled to a processor, where the processor implements a control algorithm for modulating and improving plant growth and attributes by adjusting the light emitted by light-emitting diodes.

WO2008118080 shows a promising approach in relation to artificial lighting in a greenhouse environment, however, it would still be desirable to further optimize the growth cycle, to be able to improve the growth process of a plant.

In particular, it would be desirable to store growth information to understand how the optimal growth conditions for a plant vary at various stages of the growth cycle of the plant. Such understanding would be of extreme importance for optimizing plant growth, and would allow adaptive selection of the most suitable growth regime in every stage of the growth cycle. Such adaptive control using stored growth information would enable the growth modulating system to react to changes in the uncontrolled aspects of the environment, leading to a completely new generation of intelligent greenhouses.

SUMMARY OF THE INVENTION

It is an object of the present invention to provide such adaptive control of a plant growth cycle, thereby optimizing the growth control in a situation where the environment can only be partially controlled.

According to a first aspect of the invention, the above object is achieved by a method for controlling of a growth cycle for a plant of a predetermined type comprising chlorophyll arranged in a controlled environment, to enable the plant to reach a desired growth status, the method comprising the steps of: defining a set of growth states, each of the growth states associated with at least one growth regime defining control of at least one controllable growth modulator; when in a present growth state, determining a current growth status of the plant, selecting a selected growth regime of the at least one growth regimes and controlling the at least one growth modulator according to the selected growth regime; wherein the step of selecting a selected growth regime in the present growth state is based on the desired growth status and the determined current growth status.

The invention is based on the understanding that a plant has a number of optimal growth conditions that may vary over the course of an entire plant life cycle. In order to optimize plant growth, it is crucial to identify and select the most optimal growth regime for control of the conditions in every given moment in time. The invention succeeds in doing this by selecting a growth regime based on the current growth status (i.e. the current status of the plant) and a desired growth status (i.e. a desired product which is the target of the growth cycle). In the context of the present invention, a "growth regime" is a control regime, i.e. a set of parameters defining a feedback control of at least one controllable growth modulator. Note that a growth regime is not necessarily configured to promote growth, but may be configured to "stress" the plant in order to trigger a desired development, such as a specific taste or smell.

The invention is further based on the understanding that the plant life cycle may be divided into several growth states in which the growth regime (i.e. control regime) for various growth modulators may be optimized for each particular state, again depending on the desired growth status and the current growth status.

The set of defined growth states will depend on the plant and the selected control strategy. It may be helpful to assign the states labels corresponding to observed stages in a plant development, such as germination, growing, flowering, etc. This will also be done in the following detailed description. However, in the context of the present invention, the expression "growth state" most generally refers to a state of the plant where a selection of parameters is within a defined range. For each such growth state there is one or several growth regimes (i.e. control regimes) that are considered suitable for this particular state.

A "growth status" (e.g. desired growth status or current growth status) may be defined as the property value(s) of at least one detectable property indicative of the status of the plant. Such properties may include plant height/width, stem size, growth rate, stress, properties of light reflectance, properties of fluorescence, weight, consumption of CO2, water or nutrition, plant color, size of leaves, size of flowers, number of leaves, flowers, fruits or seeds, occasions when the flowers have been exposed to pollinating insects, time in the current growth state, etc. Light reflectance is properties of light emitted by a light-emitting device and reflected by the plant. Moreover, properties of fluorescence are properties of fluorescent light from the plants, such as chlorophyll fluorescent light.

In accordance to the invention, the expression "controlled environment" should be interpreted broadly, including for example a greenhouse, a growing cabinet, or similar controlled growth environment where the plants may be subject to at least illumination of natural light. The controlled environment is thus typically an "indoor environment" comprising a transparent window or similar for allowing the natural light (such as sun) to be received by the plants. It is important to note that the "controlled" environment will never by fully controlled. To begin with, the contributions from natural light and outside temperature will vary. Also, the processes that are "controlled" will inevitably include factors outside the control of the users, including seed quality, diseases, human error, etc. It is this reality that creates a demand for the present invention, which adaptively will select the optimal growth regime in every instance.

The expression "plant of a predetermined type" typically relates to any single type of plant or a mixture of more than one type of plant having similar or combinable growth characteristics, e.g. needing a similar quantity of e.g. light for reaching a desired growth state. For reaching the desired growth status in the total growth cycle, a plant being of a specific type is of course subject to further factors influencing the growth, including for example an amount of fertilizers as well as greenhouse $CO_2$ concentrations (in case the plant grows according to a normal procedure).

Accordingly, advantages with the present invention include the possibility of more accurately predicting a growth cycle end date and a quality of the plant end product, more accurately optimizing the amount of energy used by the light system relative to the plant growth rate.

The selection of a selected growth regime may further be based on previously selected growth regimes in previous growth states. This information may be helpful, as the previously applied growth regimes will have affected the plant. An extended growth status may be defined to include not only a set of properly values, but also historical values of such properties and a sequence of previously applied growth regimes. Such an extended growth status will provide a more complete representation of what the plant is. By taking this extended growth status into account, the selection of a selected growth regime may be made more accurately with increased probability of reaching a desired growth status.

The selection of a selected growth regime may further be based on previously stored sequences of growth regimes, each such sequence being associated with a resulting growth status. The previously stored sequences of growth regimes may further include information about growth status associated with each growth regime.

Such historic knowledge for previous growth cycles of other plants may be stored e.g. in a database and includes the resulting growth status of each plant together with the sequence of growth regimes that led to that particular growth status. By storing such information, knowledge from growth cycles of many individual plants may be stored to form a database of growth history. By accessing this database, the control of growth modulators may be based on experience, leading to improved accuracy in predictability, performance and efficiency.

Such statistics may be used for selecting a selected growth regime which is a match for reaching the desired growth status. In other words, the likelihood of reaching a desired growth status is increased by selecting a growth regime that in the past has contributed to reaching this particular growth status. The method thus becomes self-learning, leading to improved performance and efficiency.

In one embodiment, selecting a selected growth regime may comprise comparing the present growth status and the desired growth status to previously stored sequences of growth regimes and finding a match. By storing sequences of growth regimes along with the growth status of the particular sequence a comparing step enables selecting a growth regime with the highest probability of resulting in the desired growth status.

According to one embodiment it may be possible to adjust the desired growth status during a growth cycle. In particular the desired growth status may be adjusted in relation to a desired growth cycle end date. Thus, in case a request is made to complete the growth cycle in a shorter (or longer) time (e.g. due to a changed demand), a different regime for growing the plants may be implemented, where the plants thus may be grown in a faster (or slower) manner.

According to one embodiment of the invention, the transition between different growth states is performed by defining a transition condition for transition from a first growth state to a second growth state, the transition condition comprising a set of predefined property values or ranges of property values of respective detectable properties of said plant, in the first growth state, comparing the current growth status with said transition condition, and if the current growth status fulfills the transition condition, transitioning to the second growth state.

Thus, the transition from one growth state to another growth state is regulated by the transition condition which has to be fulfilled in the first growth state in order to transition to the second growth state. Depending on the type of property values included in the growth status, the transition condition may include specific values or ranges.

In addition to the growth states included in the normal development of the plant, the defined set of growth states may also include one or several recovery growth states and/or a termination state.

The recovery growth state(s) comprises growth regimes especially adapted to recover a plant which is not progressing normally, e.g. due to stress. The growth regimes may be related to e.g. different levels of stress for the plant. Similar to other growth states, each recovery growth state has a transition condition (i.e. a recovery transition condition), and if the current growth status fulfills this recovery transition condition the recovery state is entered. In the recovery state, a stressed plant may be recovered before entering the next growth state, or re-entering the earlier growth state where the recovery transition condition occurred. By allowing a for example stressed plant to enter a recovery growth state, plants that otherwise may be wasted may be recovered, thus savings on valuable produce may be obtained.

The termination state represents termination of the growth cycle, and the transition condition for the termination state (i.e. an exit transition condition) will correspond to a plant which is considered to be difficult or impossible to recover. This means that the growth cycle can be terminated if the conditions are disadvantageous, avoiding waste of resources on plants that will not mature into valuable produce.

According to second aspect of the present invention, there is provided a system for controlling a growth cycle for a plant arranged in a controlled environment, wherein the system comprises an artificial light arrangement, and a control unit which is configured to control the artificial light arrangement in accordance with a growth regime selected with a method according to the first aspect of the invention. This aspect of the invention provides similar advantages as discussed above in relation to the first aspect of the invention.

The system may further comprise a set of sensors or manual data interface for acquiring a detectable property indicative of property values corresponding to growth status of said plants.

According to a third aspect of the present invention, there is provided a computer program product comprising a computer readable medium having stored thereon computer program code for performing the steps of the method according to the first aspect of the invention. This aspect of the invention provides similar advantages as discussed above in relation to the previous aspects of the invention.

The control unit is preferably a micro processor or any other type of computing device. Similarly, the computer readable medium may be any type of memory device, including one of a removable nonvolatile random access memory, a hard disk drive, a floppy disk, a CD-ROM, a DVD-ROM, a USB memory, an SD memory card, or a similar computer readable medium known in the art.

Further features of, and advantages with, the present invention will become apparent when studying the appended claims and the following description. The skilled addressee realize that different features of the present invention may be combined to create embodiments other than those described in the following, without departing from the scope of the present invention.

BRIEF DESCRIPTION OF THE DRAWINGS

The various aspects of the invention, including its particular features and advantages, will be readily understood from the following detailed description and the accompanying drawings, in which.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

Figure 1:
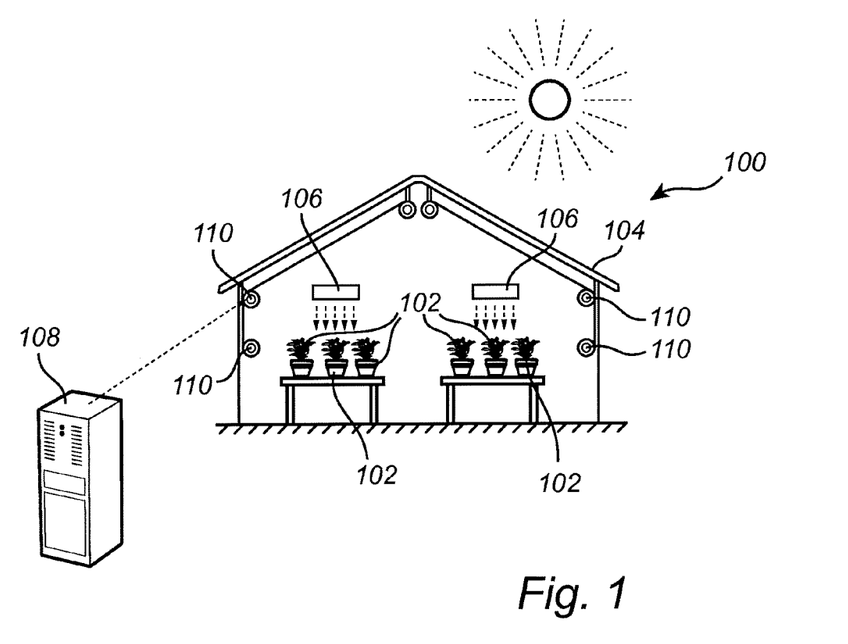
FIG. 1 shows a plant growth system according to a currently preferred embodiment of the invention.

Referring now to FIG. 1 in particular, there is depicted a system 100 according to a possible embodiment of the invention. FIG. 1 shows a plurality of plants 102, arranged in an at least partly controlled environment in the form of a greenhouse 104 typically having walls and its roof constructed of transparent structures such as of glass and/or some suitable plastic material for allowing natural light from the sun to enter the inside of the greenhouse 104. The plants may of course be another type of plants such as e.g. herbs, medicinal plants, ornamental and general crops, etc. Furthermore, the controlled environment could of course be one of a walk-in chamber or a growth cabinet depending on the type of implementation of the inventive concept. In the greenhouse 104, there is an artificial light arrangement 106 electrically connected to a control unit 108. The artificial light arrangement 104 comprises suitable artificial light sources, e.g. light-emitting diodes (LEDs), and is arranged such that light emitted by the sources is received by the plants 102. The control unit 108 may be analogue or time discrete, include a general purpose processor, an application specific processor, a circuit containing processing components, a group of distributed processing components, a group of distributed computers configured for processing, etc. The processor may be or include any number of hardware components for conducting data or signal processing or for executing computer code stored in memory. The memory may be one or more devices for storing data and/or computer code for completing or facilitating the various methods described in the present description. The memory may include volatile memory or non-volatile memory. The memory may include database components, object code components, script components, or any other type of information structure for supporting the various activities of the present description.

In order to effectively control the growth modulators a plurality of sensors 110 are arranged in or around the greenhouse 104. Such sensors may for example be configured to determine one or several conditions for the plants 102, as well as for determining current values of detectable properties of the plants, thereby determining current growth status of the plants. The sensors may for example include sensors for measuring air/soil temperature, moisture, humidity, carbon dioxide, air pressure, fertilizer levels, and/or image capturing devices (e.g. cameras) to be used for determining a growth status for the plant 102. As an alternative, or complement, to the sensors 110, there may be provided one or several manual interfaces, allowing manual input of various property values.

In addition, the greenhouse 104 may comprise controllable heating elements (not shown) as well as windows (and similar controllable ventilation arrangements) (not shown) connected to the control unit 108 for controlling the temperature within the greenhouse 104, also being dependent on a desired temperature fluctuation for the plant 102 during its growth cycle. The location of the sensors 110 are merely for illustrative purposes and not necessarily accurate. Thus, the sensors 110 may be located where most appropriate depending on the type of sensor.

Furthermore, models for the control of the growth modulators are defined. Various types of control and appropriate control schemes may be selected. In some situations, e.g. during a nursing state of a plant, static control may be preferred, while often some type of feedback control is appropriate. For such feedback control of the growth modulators, the measured growth properties are analyzed by e.g. a processor 108. The growth modulators are adjusted according to the model defined by the growth regime and the measured growth properties.

In an exemplary embodiment, the light-emitting device 104 irradiates the plants. At least part of the emitted light is reflected by the plant 102 and detected by at least one light detector (e.g. 110). The light detector 110 further detects fluorescent light from the plants 102, such as chlorophyll fluorescent light. The light detected by the light detector 110 is analyzed by the processor for determining at least one growth property. The processor determines to, depending on properties of the detected light and the model, modulate the light emitted by the light-emitting diodes, for example by adjusting the intensity or the spectral composition of the emitted light, in order to modulate or improve the growth of the plants 102.

Figure 2:
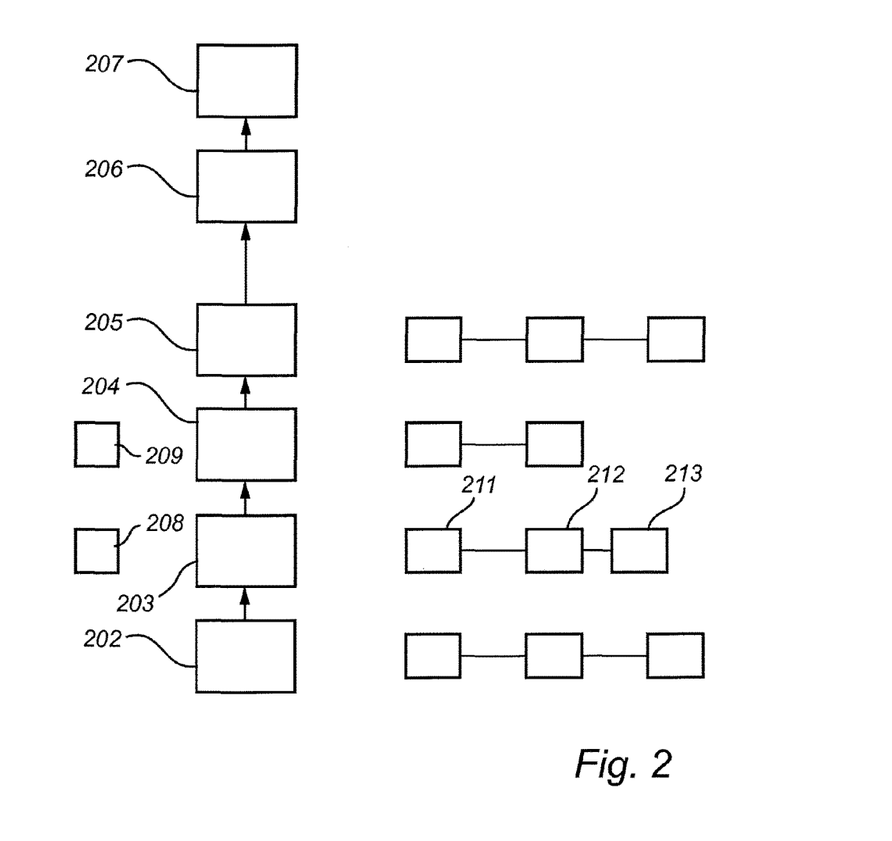
FIG. 2 provides an exemplary set of growths states according to an embodiment of the invention.

FIG. 2 shows a state model scheme of a method according to an example embodiment of the present invention. The flow chart illustrates a set of defined growth states 202-209, where each growth state is associated with at least one growth regime defining feedback control of at least one controllable growth modulator. Different growth states will have different available growth regimes, adapted for that particular growth state.

Exemplary growth states depicted in FIG. 2 are a "germination state" 202 which is a state where the plant e.g. emerges from a seed, a "nursery state" 203 where the plants may grow to a certain size, a "growing state" 204, a "flowering state" 205 where flowers of a certain quality develops, a "maturing state" 206 where e.g. a fruit is ripening, a "finish state" 207, representing the completion of the desired product, a "recovery state" 209 where a stressed plant may be recovered, and a "termination state" 208 where a growth cycle for plant, which may not recovered and/or is not economically favorable, is terminated. A stressed plant may be plant that has been exposed to an excess of light, insufficient light, light of inappropriate spectral composition, germs, too narrow distribution of plants affecting the roots, a plant that has received too much/little water and/or fertilizer etc. The exemplary growth state 203 ("nursery state") has three growth regimes 211-213 which may have attributes such as, but not limited to, "short plant" 211, "medium plant" 212, and "tall plant" 213. Other growth states may also be included, thus, the mentioned growth states herein are not limiting.

Each plant is described by its growth status, comprising property value(s) for a set of detectable properties. Such properties may include plant height/width, stem size, growth rate, stress, properties of light reflectance, properties of fluorescence, weight, consumption of $CO_2$, water or nutrition, plant color, size of leaves, size of flowers, number of leaves, flowers, fruits or seeds, occasions when the flowers have been exposed to pollinating insects, time in the current growth state, etc.

Each growth state 202-209 has a predefined transition condition, which must be fulfilled before the state can be entered. The transition conditions may be specific values or ranges of values of the properties included in the growth status. When the growth status of a plant fulfills the transition condition for a particular growth state, this growth state of the state model will be entered.

It may also be advantageous to define an extended growth status, including not only values of detectable properties, but also historical values of such properties and/or the various growth regimes that have been applied to the plant.

Note that the transition condition also may be a combination of a specific property value or range of values and a specific exposure value, such as a time duration, light exposure, water/$CO_2$/nutrition consumption, etc. For example, a transition condition may be that a plant has grown less than predefined amount during a certain time period and/or exposure, or that a plant has fewer flowers than a predefined amount after a certain time period and/or exposure. When such a transition condition is fulfilled, it is an indication that the plant is not performing appropriately, and a growth state addressing this failure to perform may be entered.

Figure 3:
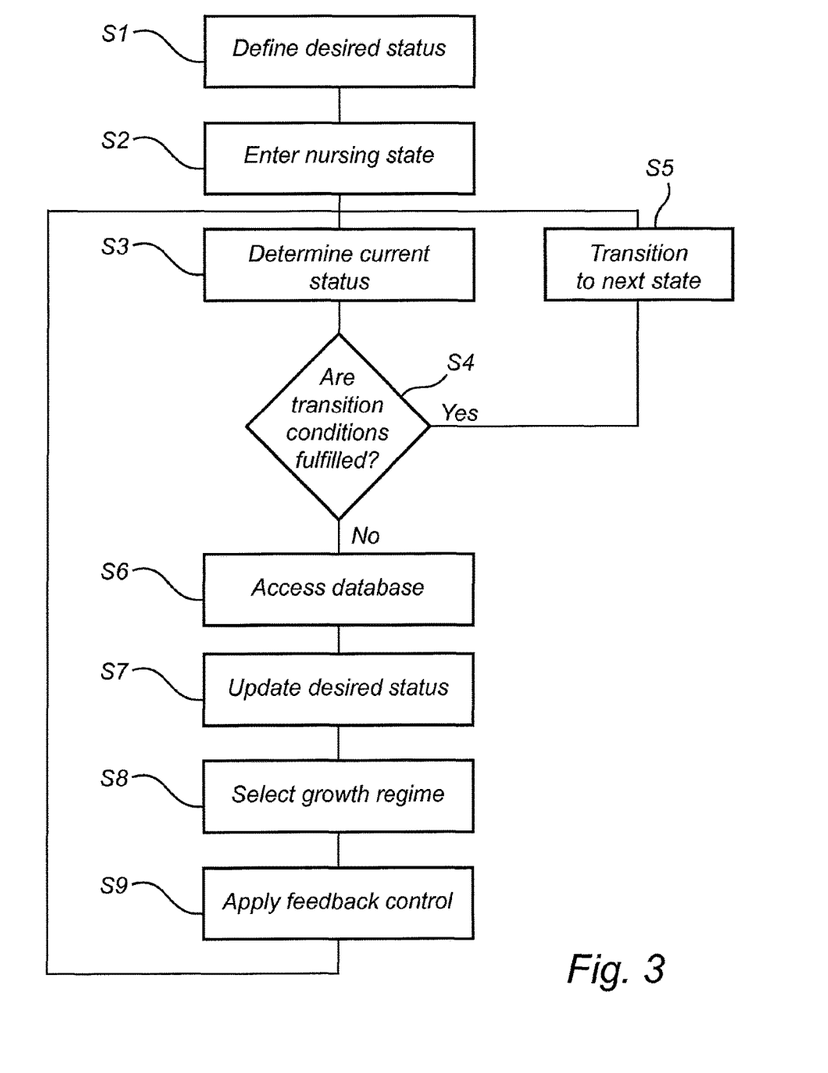
FIG. 3 provides a flow chart of the method steps according to an embodiment of the invention.

FIG. 3 shows a flow-chart describing a method according to an embodiment of the present invention.

In a first step S1 a desired growth status is defined. A desired growth status is a growth status representing the intended end product of the growth cycle, i.e. the result to be achieved in the growing process discussed herein. In some cases this will be a fully grown plant, while in other cases it may be a plant in an intermediate state, intended to continue to grow elsewhere.

In step S2, an initial growth state 202 is entered. The initial growth state is typically a "germination state" 202 or "nursing state" 203, but this will depend on the particular growth cycle. Next, in step S3, a current growth status of the plant is determined, by determining current values of the properties included in the growth status. The values may be determined by sensors 110, or be manually input by a user interface.

In the next step S4, the current growth status is compared to a set of transition conditions. If a transition condition is fulfilled, the process will in step S5 enter the next growth state (e.g. a "nursery state" 203). If no transition condition is fulfilled, the process continues to step S6-S8 where a growth regime is selected based on the desired growth status, the current growth status, and optionally previously stored sequences of growth regimes.

Step S6 may include access to a database storing previous growth regime sequences and their resulting growth statuses. Step S6 will be further explained with reference to FIG. 4.

After a growth regime has been selected S8, feedback control is applied in step S9 to control at least one growth modulator for adjusting the growth environment for the plant. The selection of growth regime affects the applied feedback control. As mentioned above, a growth modulator may be light spectral composition, light intensity, temperature, level of fertilizer, $CO_2$ level, water vapor pressure in the surrounding air, air movement, watering, bees for pollination etc. After a predetermined time has lapsed, the process returns to step S3, where again the current status is determined, and steps S4-S8 are repeated.

It is noted that the next growth state in step S5 may be a "recovery state" 209 or a "termination state" 208.

Optionally, the desired growth status may be tuned during the growth cycle. Thus, in an optional step S7 the desired growth status may be updated. This way, the duration of the growth cycle may be decreased or increased, or a change in specific product demand from the market may be taken into account in the growth process.

Figure 4:
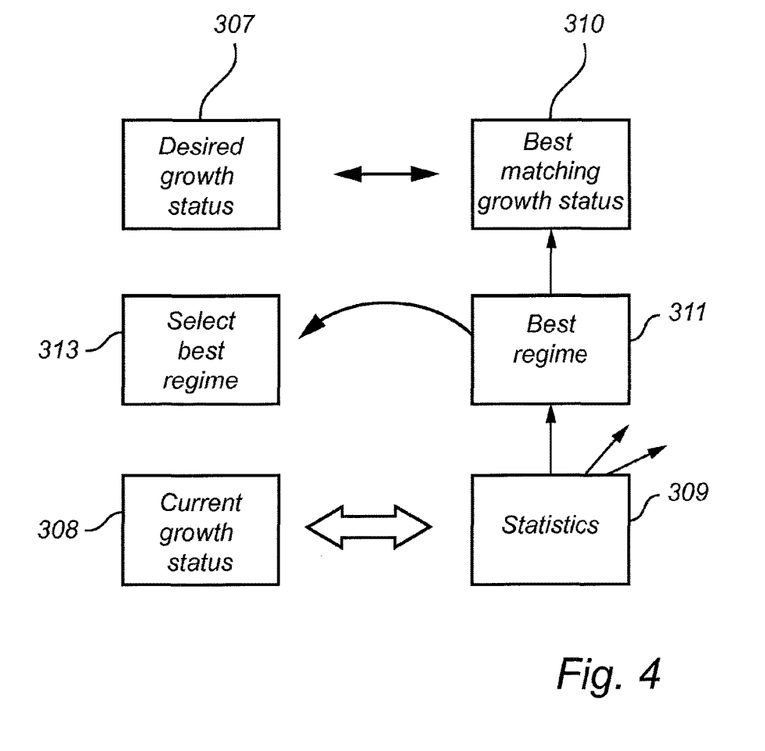
FIG. 4 is an exemplary schematic view of a growth regime selection scheme.

FIG. 4 shows a schematic view of a selecting of a growth regime. When in a growth state of a growth cycle, a current growth status 308 is determined, as indicated by S3 in FIG. 3. Optionally, as discussed above, an extended growth status may be determined. The extended growth status may include historical values of detectable properties and/or previously selected growth regimes. Still in the same growth state, a "best" growth regime is selected in 313 (step S8 in FIG. 3). As mentioned above, the step S8 of selecting a growth regime is based on the desired growth status 307 and the current growth status 308 or extended growth status.

The selection is here based on statistics 309, including e.g. previously stored sequences of growth regimes and their resulting growth statuses. With the current growth status 308 as the starting point, the growth regime 311 which has historically resulted in a growth status being a closest matching growth status 310 compared to the desired growth status 307 can then be selected 313. Thus, in this case a selected growth regime can be chosen based on previously successful growth regime sequences.

Furthermore, transition conditions of previous growth regime sequences may be stored. In this way, it may be possible to use the previously stored transition conditions to further improve the selection of a growth regime. As mentioned previously, if a plant is in a current growth state and a growth regime is to be selected, the previously stored growth regime sequences may be used for finding an appropriate growth regime to be selected. However, by also including the previous transition conditions of previous growth regime sequences and also of the current growth regime sequence, it may be possible to obtain a more flexible selection process. For example, it may be desirable to tune the transition conditions for a particular transition between states such that it may affect the selection of a growth regime.

The matching of growth statuses will now be explained with reference to table 1 below, showing an example with a plant currently being in a particular growth state with a current growth status and a previous growth status. There is further information about two previous plants growth cycles (P1 and P2) in this particular growth state. This information also includes a current growth status and a previous growth status. Further, the information about P1 and P2 also includes the selected growth regime (X or Y) and the resulting status.

TABLE 1

Example of growth regime matching

|  | Current plant | P1 | P2 |
| --- | --- | --- | --- |
| Desired status | Good | | |
| Current status | T: 3 | T: 3 | T: 4 |
|  | NF: 8 | NF: 10 | NF: 6 |
| Previous status | Str: Y | Str: Y | Str: N |
|  | T: 8 | T: 8 | T: 6 |
| Selected Regime | ? | X | Y |
| Resulting status |  | Good | Good |

For simplicity, the desired growth status and resulting growth status are simply given as "good". This growth status may of course typically comprise a set of values on various scales. Again for simplicity, the current status and previous status only include a small number of property values (current status includes "time in state", T, and "number of flowers", NF, while previous status includes "stress detected", STR, and "time in state", T). These examples may be seen as a selection of a larger number of available detectable properties.

In this particular example, the selected regime for the plant will be regime X, because the matching of the current status and previous status is better with P1 than with P2. For example, the "stress detected" and "time in state" are matched with P1 rather than with P2.

Note that different growth property values (e.g. number of flowers, time in state, reflectance property, etc.) may have different weights when performing a match. For example, "number of flowers" may in some cases be more important than "time in state". Furthermore, statistics regarding how accurate an obtained matching was done may be stored and used in future matching processes for improving accuracy, and for facilitating a self-learning method.

Furthermore, in controlling the growth process of the plants, specifically in relation to optimizing the growth process in relation to a just-in-time concept by e.g. tuning the desired growth status as explained with reference to FIG. 3, it may be possible to make additional considerations, i.e. to be included in the determination of light/temperature control, etc. within the greenhouse 104. Such considerations may for example relate to the actual size of the greenhouse, e.g. relating to the number of plants 102 arranged in the greenhouse 104 as well as the number of persons working within the greenhouse 104. Similar considerations may be made in regards to e.g. a grower/producer operating a plurality of greenhouses, e.g. both relating to energy consumption (total peek consumption for all of the plurality of greenhouses operated by the same grower/producer) as well as in relation to the number of persons servicing (e.g. general operation when growing plants) the plurality of greenhouses.

Still further, also logistical considerations may be taken into account when controlling the growth process within the one of plurality of greenhouses. That is, from a logistical perspective there are generally limitations (trucks, personnel, etc.) in relation to the number of plants that may be transported each and every day. As such, this type of consideration may be taken into account by the system 100 such that the number of plants having reached the desired completion state in some sense matches the capacity of the logistical arrangement used for transporting plants to e.g. the factory/store/etc.

Furthermore, in case different types of plants are grown by the grower, it may be possible to use the knowledge of the growth process for each of the type of plants, such that a desired mixture of different types of plants may be ready for delivery at the same time, thus possibly minimizing transportation to a specific "consumer" (e.g. again being e.g. a factory/store/etc.).

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps. Additionally, even though the invention has been described with reference to specific exemplifying embodiments thereof, many different alterations, modifications and the like will become apparent for those skilled in the art. Variations to the disclosed embodiments can be understood and effected by the skilled addressee in practicing the claimed invention, from a study of the drawings, the disclosure, and the appended claims. Furthermore, in the claims, the word "comprising" does not exclude other elements or steps, and the indefinite article "a" or "an" does not exclude a plurality.

The invention claimed is:

1. A computer implemented method for controlling of a growth cycle for a plant of a predetermined type comprising chlorophyll arranged in a controlled environment, to enable said plant to reach a desired growth status, said method comprising the steps of:
    defining a set of growth states, each of said growth states being a state of said growth cycle, wherein a selection of property values of respective detectable properties of said plant is within a defined range, and each of said growth states being associated with a plurality of growth regimes defining control of an artificial lighting arrangement for adjusting light spectral composition and/or light intensity; and
    when in a present growth state:
        determining, by means of a plurality of sensors, a current growth status of said plant, wherein said current growth status comprises a set of said property values of respective detectable properties of said plant, and
        selecting a growth regime of said plurality of growth regimes and controlling said artificial lighting arrangement according to said selected growth regime,
        wherein the step of selecting a growth regime in said present growth state is based on said desired growth status, said determined current growth status, and on previously selected growth regimes in previous growth states.

2. The method according to claim 1, wherein the step of selecting a growth regime further is based on previously stored sequences of growth regimes, each such sequence being associated with a resulting growth status.

3. The method according to claim 2, wherein said previously stored sequences of growth regimes further comprise information about growth status associated with each growth regime.

4. The method according to claim 1, wherein the step of selecting a growth regime further comprises comparing said current growth status and said desired growth status to previously stored sequences of growth regimes and finding a viable match.

5. The method according to claim 1, further comprising adjusting said desired growth status during said growth cycle.

6. The method according to claim 1, further comprising:
    defining a transition condition for transition from a first growth state to a second growth state, said transition condition comprising a set of predefined property values or ranges of property values of respective detectable properties of said plant;
    in said first growth state, comparing said current growth status with said transition condition; and,
    if the current growth status fulfills said transition condition, transitioning to said second growth state.

7. The method according to claim 6, wherein said transition condition is a recovery transition condition and said second growth state is a recovery state.

8. The method according to claim 6, wherein said transition condition is an exit transition condition, and second growth state is a termination state representing termination of said growth cycle.

9. The method according to claim 1, wherein said control is feedback control.

10. A system for automatically controlling a growth cycle for a plant arranged in a controlled environment, wherein the system comprises:
    an artificial light arrangement;
    a set of sensors arranged to acquire a detectable property indicative of a growth status of said plant; and
    a control unit configured to control said growth cycle according to the steps of claim 1.

11. The system according to claim 10, wherein from defined transition conditions for transition from a first growth state to a second growth state, said transition condition comprising at least one predefined property value of a respective detectable property indicative of said current growth status of the plant, the control unit is further configured to:
    in said first growth state, determine at least one of said at least one current property value of said respective detectable property; and
    if said at least one current property value corresponds to said at least one predefined property value, control a transition to said second growth state.

12. A computer program product comprising a computer readable medium having stored thereon computer program means for a system for automatically controlling a growth cycle for a plant, wherein the computer program product comprises code for performing the steps according to claim 1.

* * * * *